United States Patent [19]
Scott et al.

[11] Patent Number: 5,593,450
[45] Date of Patent: Jan. 14, 1997

[54] OVAL DOMED SHAPED PATELLA PROSTHESIS

[75] Inventors: Richard D. Scott, Dedham; Thomas S. Thornhill, Dover; John Slamin, Wrentham, all of Mass.

[73] Assignee: Johnson & Johnson Professional, Inc., Raynham, Mass.

[21] Appl. No.: 396,181

[22] Filed: Feb. 27, 1995

[51] Int. Cl.[6] .................................................. A61F 2/38
[52] U.S. Cl. .............................................. 623/20; 623/18
[58] Field of Search ................................. 623/16, 18, 20

[56]     References Cited
        U.S. PATENT DOCUMENTS

| 4,151,615 | 5/1979 | Hall | 623/20 |
| 5,181,924 | 1/1993 | Gschwend et al. | 623/20 |
| 5,383,937 | 1/1995 | Mikhail | 623/20 |

FOREIGN PATENT DOCUMENTS

| 3332354 | 3/1985 | Germany | 623/20 |

*Primary Examiner*—David Isabella
*Attorney, Agent, or Firm*—Joseph F. Shirtz

[57]     ABSTRACT

An improved knee prosthesis disclosed that includes a patella for positioning in a trochlear groove formed by two condyles of a femoral component. The novel patella of the disclosure has an elliptical outer periphery and presents an articulating surface to the femoral component for sliding engagement with a trochlear groove formed between the condyles of the femoral component. A side opposite the articulating surface has extending therefrom three posts which enhance the attachment of the patella prosthesis to the patella bone. In one embodiment of the invention an undercut area which is cut into the bone contacting surface of the prosthesis presents an overhang or undercut to the bone in order to enhance cement fixation. The overhang is formed by an outer defining wall which is positioned at an angle to a bottom surface of the recessed overhang area of between 50° and 75°.

11 Claims, 2 Drawing Sheets

FIG. 1A
PRIOR ART
FIG. 1B
PRIOR ART
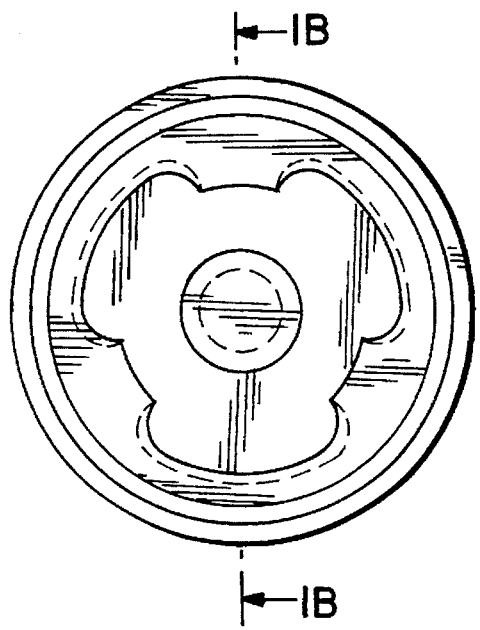
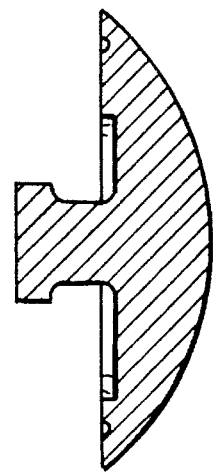
FIG. 2A
PRIOR ART
FIG. 2B
PRIOR ART
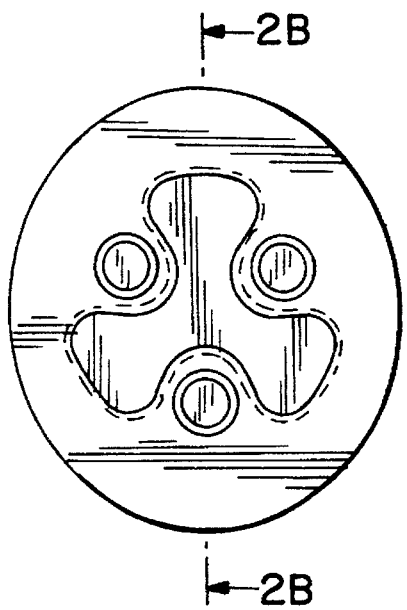
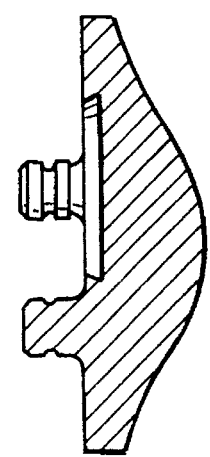

OVAL DOMED SHAPED PATELLA PROSTHESIS

FIELD OF THE INVENTION

This invention relates to medical devices and in particular to improved joint prosthesis for use in human joint replacement.

BACKGROUND OF THE INVENTION

Total knee arthroplasty has been a very successful procedure for the treatment of various types of joint disease. See, for example, "The Effect of Trochlear Design on Patellofemoral Shear and Compressive Forces in Total Knee Arthroplasty", W. J. Petersilge, M.D. et al., Clinical Orthopaedics and Related Research, Number 309, pp 124–130. This article has described in detail the various types of patella prosthesis and their affects on the shear forces in knee studies. This reference is incorporated herein in total by reference.

In particular patella prosthesis having a domed shape contact surface and round outer perimeter have been in use since the early 1970's. The advantage of such prosthesis are the simple instrumentation for insertion, the implant is positionable on the patella bone based on anatomy of the patient and can be placed medial to the center of the bone to improve tracking, the device is insensitive to poor alignment and contact area is increased when used with a deep conforming trochlear groove in a femoral component. The increase of contact area in a trochlear groove reduces the contact stress as the force is the same, however, the area over which the force is spread is increased with the increased contact area.

However, such round shaped prosthesis have a relatively poor ability to cover the cut surface of the patella. That is, the surface of the patella that is resected during surgery in order admit the prosthesis.

Patellas of this type are shown in prior art FIG. 1A and FIG. 1B.

In the early 1980's the patella prosthesis was modified along an oval biconcave form as shown in prior art FIG. 2. This modification provided better bone coverage due to a more anatomical shape and the patella forces were transferred from the dome portion of the patella at flexion angles below 75° to the peripheral concave surfaces at patella flexion angles above 75°. The three peg attachment design on the surface of the patella increased the contact surface also preserved blood supply and bone in the patella.

It has now been found that by providing a patella prosthesis with an oval periphery and a domed contact surface, i.e., substantially consistent radius, that reduced contact stress as well as increased bone coverage of the oval could be provided.

SUMMARY OF THE INVENTION

The invention calls for an oval shaped patella prosthesis having a domed contact surface which is used in connection with a deep trochlear groove on a femoral component. In this way contact stresses are significantly reduced as compared to a biconcave patella used with a shallow groove as shown in the prior art. The knee prosthesis is of the type having a femoral component that includes two condyles as articulating surfaces. The two condyles meet to form a deep trochlear groove and ride on a tibial component that articulates with respect to the femoral component. A patella prosthesis for sliding engagement with the trochlear groove is provided in the prosthesis. The patella portion of the prosthesis has an oval overall perimeter shape and a domed articulating surface. The articulating surface is the surface which comes in contact with the sides of the condyle which meet to form the trochlear groove. On the side opposite the domed shape contacting surface the patella has at least one post and preferably three posts extending for attachment to the patella bone after resection. That is, the patella bone is resected to receive the prosthesis post. Further, an area of undercut, that is, having a short overhang may be provided on the surface opposite the contact surface in order to increase the degree of fixation in a cement attachment procedure. The undercut provides an area for the cement to grab the prosthesis and attach the prosthesis to the resected patella.

BRIEF DESCRIPTION OF THE DRAWINGS

FIG. 1A is a prior art device showing the domed shaped patella prosthesis having a circular periphery;

FIG. 1B is a cross-sectional view taken along line 1B—1B of FIG. 1A;

FIG. 2A is a prior art drawing of a biconcave patella prosthesis;

FIG. 2B is a cross-sectional view taken along line 2B—2B of FIG. 2A;

DESCRIPTION OF THE PREFERRED EMBODIMENT

Figure 3:
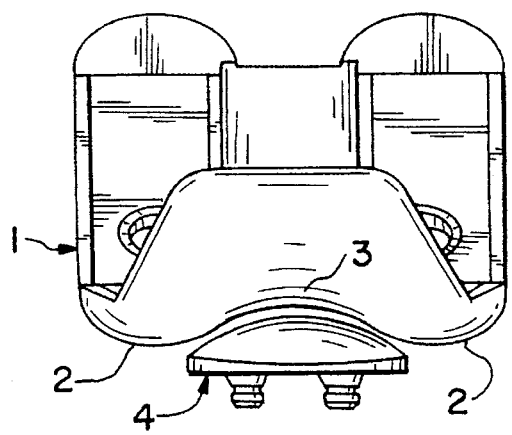
FIG. 3 is a diagram of a knee prosthesis shown in the femoral component and its interaction with the patella prosthesis.

FIG. 3 shows a representation of the femoral component of a knee prosthesis with the patella portion of the prosthesis in place and riding thereon in the trochlear groove. The prosthesis has a femoral component 1 having condyles 2 formed thereon. The condyles define a trochlear groove 3 in which rides a patella prosthesis 4. The femoral component may be of any of the many types currently available or may be of a type modified to have a deep trochlear groove 3 in order to provide the significant contact area at the interface with the patella prosthesis 4. The femoral component is preferably made out of cobalt chrome alloy and the patella prosthesis is preferably made out of ultra high molecular weight polyethylene ("UHMWPE").

Figure 4:
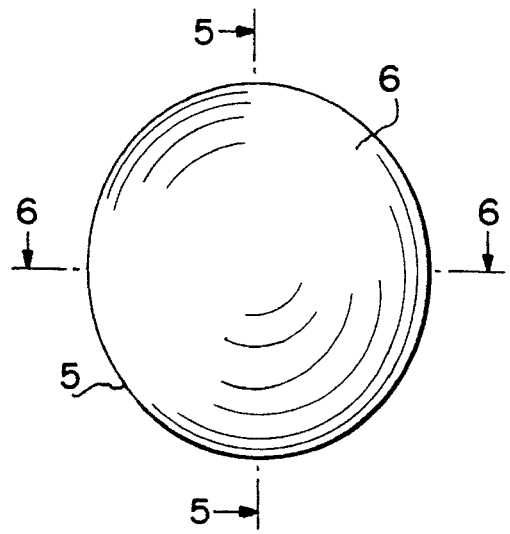
FIG. 4 is a plan view of the contact surface of the patella of the invention.
Figure 5:
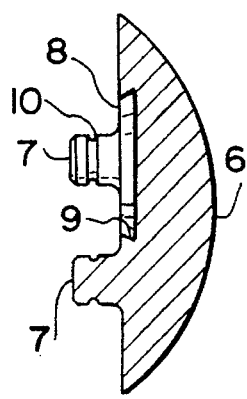
FIG. 5 is a transverse cross-sectional view along minor axis line 5—5 of FIG. 4.
Figure 6:
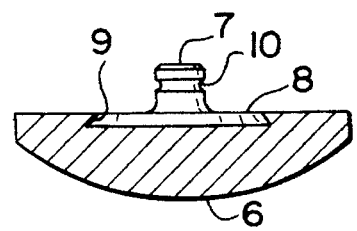
FIG. 6 is a longitudinal view along major axis line 6—6 of FIG. 4.

FIG. 4 shows a plan view of the contact surface of the patella prosthesis. The outer periphery 5 of the patella prosthesis of the invention is non-circular, that is, preferably elliptical in shape. The articulating surface 6 is preferably of a dome shaped, that is, of a shape of constant radius of, for example, one inch. This constant radius in combination with the oval shape of the outer periphery 5 requires that the patella prosthesis have a variable edge thickness along the outer periphery. As is seen in FIG. 5 a small edge is formed as the curvature is not sufficient to bring the articulating surface down to the surface opposite the articulating surface in the narrow transverse direction of the patella. However FIG. 6 shows the minimum dimensional aspect of such an edge.

Figure 7:
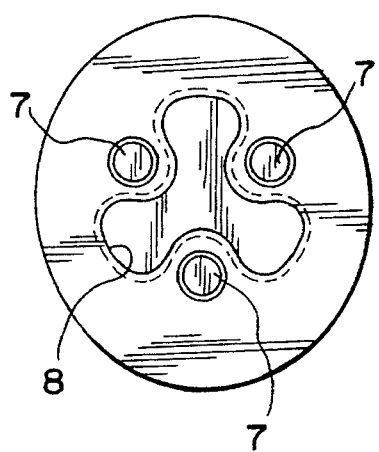
FIG. 7 is a plan view of the side opposite the contact surface of the patella prosthesis of the invention.

Extending from the side opposite the articulating surface are three posts 7 (FIG. 7) that provide additional fixation for the device in the bone. These posts are positioned in a triangular shape as seen in FIG. 6 with the base of the triangle extending parallel to the narrow direction of the ellipse that forms the outer periphery 5. The preferred embodiment has the post position at the apexes of an equilateral triangle centered roughly within the outer periphery of the prosthesis.

An undercut area 8 is provided in the surface opposite the articulating surface. The undercut area 8 is sunken into the patella prosthesis and is defined by an outer periphery that includes an overhang 9 in order to provide an area of increased cement fixation. In a representative prosthesis having a dome radius of approximately one inch the representative dimensions are as follows: the minimum axial distance of the ellipse is approximately 1.1 inches and the maximum axial distance of the ellipse is approximately 1.25 inches. The post 7 extend approximately 0.2 inches above the back surface or surface opposite the articulating surface of the patella prosthesis. The post may be provided with a slight annular cut 10 in order to increase the fixation to the bone. The undercut angle of the overhang 9 may range from 50° to 75° and is preferably 67.5°. The undercut area is recessed within the back surface of the patella prosthesis by approximately 0.055 inches.

What we claim is:

1. In a knee prosthesis having a femoral component that includes two condyles as articulating surfaces, a tibial component that articulates with respect to said femoral component and a patella prosthesis for sliding engagement with a groove formed between said condyles, the improvement comprising said patella prosthesis having a non-circular outer periphery and a contact surface of substantially constant spherical radius terminating at said non-circular periphery for contacting said groove in sliding engagement.

2. The improvement according to claim 1 further including at least one post extending from an attachment side of said patella prosthesis opposite said contact side to provide fixation to a resected patella.

3. The improvement according to claim 2 wherein there are three posts.

4. The improvement according to claim 2 wherein said attachment side defines an undercut area to provide an attachment for cement fixation of said patella prosthesis to a resected patella.

5. The improvement according to claim 4 wherein said undercut area is defined in part by an overhang wherein said overhang is comprised of a wall extending at an angle between 50° and 75° with a bottom surface of said undercut area.

6. The improvement according to claim 5 wherein said wall forms an angle of approximately 67½° with the bottom of said undercut area.

7. The improvement according to claim 1 wherein the patella prosthesis has an outer perimeter of substantially elliptical shape.

8. The improvement according to claim 1 wherein said contact side of said patella prosthesis has a radius of between ¾ of an inch and 3 inches.

9. The improvement according to claim 1 wherein said radius is approximately one inch.

10. The improvement according to claim 1 wherein said patella prosthesis is formed of ultra high molecular weight polyethylene.

11. In a knee prosthesis having a femoral component that includes two condyles as articulating surfaces, a tibial component that articulates with respect to said femoral component and an ultra high molecular weight polyethylene patella prosthesis for sliding engagement with a groove formed between said condyles, the improvement comprising said patella prosthesis having a non-circular outer periphery and a first side for contact with said groove, said first side having a convex surface terminating at said non-circular periphery, said convex surface defining a substantially constant spherical radius of curvature for contacting said groove in sliding engagement, a second bone contacting side having extending therefrom at least three posts for fixation of said patella prosthesis to a resected patella bone and said bone contacting side further including an undercut area defined by an angularly position wall that defines an angle with a bottom of said undercut area of between 50° and 75°.

* * * * *